United States Patent
Teuschl et al.

(10) Patent No.: US 10,227,712 B2
(45) Date of Patent: Mar. 12, 2019

(54) PRODUCT MADE OF NATIVE SILK FIBRES

(71) Applicant: Andreas Teuschl, Vienna (AT)

(72) Inventors: Andreas Teuschl, Vienna (AT); Martijn Van Griensven, Vienna (AT); Heinz Redl, Vienna (AT)

(73) Assignee: MorphoMed GmbH, Vienna (AT)

( * ) Notice: Subject to any disclaimer, the term of this patent is extended or adjusted under 35 U.S.C. 154(b) by 674 days.

(21) Appl. No.: 14/431,479

(22) PCT Filed: Sep. 27, 2013

(86) PCT No.: PCT/EP2013/070213
§ 371 (c)(1),
(2) Date: Mar. 26, 2015

(87) PCT Pub. No.: WO2014/049129
PCT Pub. Date: Apr. 3, 2014

(65) Prior Publication Data
US 2015/0275398 A1  Oct. 1, 2015

(30) Foreign Application Priority Data

Sep. 27, 2012 (EP) .................................... 12186282

(51) Int. Cl.
| | |
|---|---|
| *D01C 3/02* | (2006.01) |
| *A61L 27/36* | (2006.01) |
| *A61L 27/38* | (2006.01) |
| *A61B 17/04* | (2006.01) |
| *A61L 27/22* | (2006.01) |
| *A61L 27/58* | (2006.01) |
| *D04B 1/14* | (2006.01) |

(52) U.S. Cl.
CPC .............. *D01C 3/02* (2013.01); *A61B 17/04* (2013.01); *A61L 27/227* (2013.01); *A61L 27/3604* (2013.01); *A61L 27/3687* (2013.01); *A61L 27/38* (2013.01); *A61L 27/58* (2013.01); *D04B 1/14* (2013.01); *A61L 2430/10* (2013.01); *D10B 2401/061* (2013.01); *D10B 2401/063* (2013.01); *D10B 2401/12* (2013.01); *D10B 2403/033* (2013.01); *D10B 2509/00* (2013.01)

(58) Field of Classification Search
CPC ......... C07K 14/43586; D06M 2101/12; D01C 3/02; D04B 1/14; A61L 27/227; A61L 27/58; A61L 27/3687; A61L 27/38; A61L 27/3604; A61L 2430/10; A61B 17/04; D10B 2401/12; D10B 403/033; D10B 509/00; D10B 401/061; D10B 401/063
See application file for complete search history.

(56) References Cited

FOREIGN PATENT DOCUMENTS

| FR | 2528076 A1 | 12/1983 |
| JP | 1229803 A | 9/1989 |
| JP | 2269870 A | 11/1990 |

OTHER PUBLICATIONS

Altman, Gregory H. et al., "Silk-based biomaterials" Biomaterials 24 (2003) 401-416.

(Continued)

*Primary Examiner* — Elizabeth M Cole
(74) *Attorney, Agent, or Firm* — Edwin S. Flores; Daniel J. Chalker; Chalker Flores, LLP

(57) ABSTRACT

Disclosed is a method for the production of three-dimensional silk products, wherein native silk fibers are formed to a three-dimensional silk product and the silk product formed is subjected to a degumming step wherein a borate buffer is used as degumming agent and wherein the silk product formed is preferably contacted with an aqueous ethanol buffer prior to the degumming step.

14 Claims, 9 Drawing Sheets

(56) References Cited

OTHER PUBLICATIONS

Dewair, Mahmoud et al., "Use of immunoblot technique for detection of human IgE and IgG antibodies to individual silk proteins" J. Allergy Clin. Immunol. Oct. 1985, 537-542.
Horan, Rebecca L. et al., "Yarn design for functional tissue engineering" Journal of Biomechanics 39 (2006) 2232-2240.
Mondal, M. et al., "The silk proteins, sericin and fibroin in silkworm, Bombyx mori Linn.,—a review" Caspian J. Env. Sci. 2007, vol. 5 No. 2 pp. 63-76.
Wolbank, Susanne et al. "Dose-Dependent Immunomodulatory Effect of Human Stem Cells from Amniotic Membrane: A Comparison with Human Mesenchymal Stem Cells from Adipose Tissue" Tissue Engineering vol. 13, No. 6, 2007, 1173-1183.
Altman G H et al: "Silk-based biomaterials", Biomaterials, Elsevier Science Publishers BV., Barking, GB, vol. 24, No. 3, Feb. 1, 2003 (Feb. 1, 2003), pp. 401-416.
Database WPI, Week 201273, Thomson Scientific, London, GB; AN 2012-N61584 & CN 102 605 439 A (Shaoxing Arts&Sci Acad) Jul. 25, 2012 (Jul. 25, 2012).
Jiang P et al: "Tensile behavior and morphology of differently degummed silkworm (*Bombyx mori*) cocoon silk fibres", Materials Letters, North Holland Publishing Company. Amsterdam, NL, vol. 60, No. 7, Apr. 1, 2006 (Apr. 1, 2006), pp. 919-925.
PCT/EP2013/070213 International Preliminary Report on Patentability dated Jan. 15, 2015.
Database IWPI Week 198617 Thomson Scientific, London, GB; AN 1986-109959 xP002693463, & JP 61 052280 A (Japan Synthettc Rubber Co Ltd) Mar. 14, 1986 (Mar. 14, 1986).
EP 12186282.5 Extended European Search Report dated Mar. 18, 2013.
PCT/EP2013/070213 Search Report and Written Opinion dated Sep. 23, 2014.

PRODUCT MADE OF NATIVE SILK FIBRES

The present invention relates to the field of silk processing, specifically for providing silk material for medical use.

Historically, silk has been used in biomedical sutures for decades, where potential host immune responses have been observed. This may be the major concern with the use of silks that have led to its disregard for biomedical applications in the past. The main cause for eliciting immune response activation has been associated with sericin (reviewed in: Altman et al., Biomaterials 24 (2003), 401-416). Therefore, the adequate removal of sericin from raw silk is a critical step in the preparation of silk for tissue engineering and regenerative medicine applications to avoid biocompatibility problems.

In most cases silkworm silk, is obtained from the cocoons of the larvae of the mulberry silkworm *Bombyx mori*. The single silkworm cocoon fibre consists of two cores of fibroin strands surrounded by a glue-like protein called sericin, which fixes the fibroin fibres to each other. Fibroin and sericin account for about 75 and 25% wt., respectively.

Morphologically, silk fibroin is characterized by its highly oriented and crystalline fibrous structure. This structure is responsible for its insolubility in most solvents such as water, ethanol, dilute acids and bases. In contrast to fibroin the globular protein sericin is readily soluble in aqueous solvents. In textile industry the removal of sericin is also of great interest because the lustre of silk clothes is concealed by sericin. Therefore, research groups working on silk are not restricted to the biomaterial field but also the textile industry searches for optimal degumming methods. This fact leads to the existence of various degumming methods, including alkaline solutions w/o detergents, urea, tartaric acid, citric acid, or enzymes, such as papain or endopeptidase. The possibility to use boric acid in combination with borate salts as degumming agent has been described in the field of textile engineering. In these studies borate buffers were used to degum unprocessed raw silk fibers alone (Jiang et al. Materials Letters 60/7 (2006), 919-925) or in combination with a surfactant agent (JP 2 269870 A) or as a so-called "scouring agent" for single fibers or woven fabrics. In the latter case borate buffers were used to scour the surface of the fibers to make it accessible for additional textile engineering processes such as bleaching, dyeing, etc. without the purpose to complete removal of sericin (JP 1 229803 A). Such products therefore still contain a high amount of sericin (e.g. more than half of total sericin is still present in the product). The incomplete removal of sericin would be insufficient for the medical field due to the elicitation of immunological reactions from residual sericin. Accordingly, it is not relevant for the present field of application.

Due to its high versatility and consistent functionality borate buffers are traditionally used in many biochemical and biotechnological applications. In this context, it has to be noted that borate buffers have been used to keep the pH-value in an optimal working range of the specific protease in enzyme-based degumming methods (CN 102 605 439 A (abstract)). This means that here the buffer is not used as a degumming agent itself but as an agent to provide the optimal working range in terms of pH for the degumming protease. In a similar way boric acid has been used to control the pH in textile engineering degumming processes using soaps (FR 2 528 076 A1).

The classical way of degumming is the boiling of the raw silk in alkaline solutions w/o detergents that assist in removing the sericin from the fibrous structure. It may be underlined that it is common to use 0.02 M sodium carbonate solution at 100° C. for 30-60 min to accomplish degumming, especially in the tissue engineering research field. Often, this alkaline degumming is carried out as batch treatment using soaps or detergents in addition to alkali.

However, different studies showed that the removal of sericin causes the silk fibre to fray and weakens its structural property, making it very difficult to textile engineer (e.g. knit or braid) them into scaffolds for tissue engineering applications (Liu et al. J. Biomed. Mater. Res. B Appl. Biomater. 82 (2007), 129-138). Therefore in some studies the silk scaffold is fabricated in advance and then the degumming process is performed (Fan et al., Biomaterials 30 (2009), 4967-4977; Fan et al., Biomaterials 29 (2008), 3324-3337; Chen et al., Biomaterials 29 (2008), 3683-3692). But it has to be noticed that the scaffold basis of all these studies are "plain" meshes (Chen et al., Biomaterials 29 (2008), 3683-3692) of thicknesses not exceeding 500 µm. Moreover, the described meshes are characterized by low levels of geometrical hierarchy, e.g. simple textile knitting techniques. Compared to higher ordered textile engineered scaffolds the single silk fibers are quite good exposed to the degumming solution and can therefore be degummed using the classical sodium carbonate solutions (see FIGS. 11A and 11B).

A labour-intensive option to enhance the processing characteristics of sericin-free fibres was proposed by Liu et al., 2007. In this study a method to replace sericin with gelatin by chemical cross-linking sericin-free silk fibres with gelatin is described.

Altman et al. (Biomaterials 23 (2002), 4131-4141 explored the potential of native silk fibroin fibres (yarns) as 3D scaffolds for tissue engineering of anterior cruciate ligaments (ACL) in cultures with dynamic mechanical loading: After sericin extraction, the silk fibroin fibres were cabled into 6-cord wire-rope matrices with improved elasticity without sacrificing tensile strength when compared to an equivalent matrix formed from parallel fibres. This matrix had a hierarchal structure similar to that of collagen fibers in the native ACL and the mechanical properties were comparable to that of the native human ACL with respect to strength, stiffness, yield point, and percentage elongation at break. In addition, the wire-rope geometry increased surface area for cell attachment and extracellular matrix (ECM) deposition and minimized mass transfer limitations, all of which contribute to an enhanced neo-tissue formation. The silk fibroin scaffolds supported the attachment, spreading, proliferation and differentiation of adult human bone marrow derived mesenchymal stem cells (MSCs).

Despite the emergent use of silk in tissue engineering applications and a lot of research in the degumming process by biomedical and industrial research groups there is still a lack of knowledge about options to degum textile engineered constructs of high geometrical hierarchies. Therefore there is currently no degumming method available that is capable to remove sericin from a compact and highly-ordered raw *Bombyx mori* silk-fibre matrix e.g. intended for anterior cruciate ligament tissue engineering.

Quite in contrast, the provision of silk material for medical uses almost exclusively employs complete dissolution of the silk fibres in aqueous systems, followed by reprocessing the silk solution into desired material formats, e.g. by spinning, electrospinning, casting from aqueous or organic solvent systems, gelation, foaming, etc. (Vepari et al., 2007, U.S. Pat. No. 5,252,285 A).

However, these reprocessed silk materials from fibroin solutions differ from the natural (native) inherent silk structures, such as decreased mechanical strength. On the other hand, silk fibres have been used most extensively as sutures for wound ligation; however, the fibres have to be degummed before application, due to the adverse effects caused by sericin (Kaplan et al., Biomaterials 24 (2003), 401-416). The vast majority of the biocompatibility problems of silk sutures are reported with virgin silk, in which sericin still covers the core silk fibroin fibers. The induction of asthma and an upregulation of Immunoglobulin E levels could be observed in patients sutured with virgin silk. In a study of Dewair et al. (J. Allergy Clin. Immunol. 76 (1985), 537-542) the peak levels of specific IgE as well as degree of positive reaction in silk sensitive patients could be seen in the groups with the highest sericin content (in the tested silk samples) in the skin test. Furthermore, it could be demonstrated that the activation of inflammatory cells including macrophages around virgin silk fibers, while in the control groups of sericin-free or gelatin-coated fibroin fibers, no activation was seen. It is clear that biomaterials which are implanted should not cause such foreign body response. Accordingly, biomaterials made of silk must be free of sericin. However, due to the negative properties of degummed silk fibres in the process of forming final biomaterials (e.g. ligatures), especially three dimensional biomaterials, improved methods are needed to provide biomaterials based on silk. These methods should enable a robust, reproducible and reliable production method; on the other hand, the products must be essentially free from sericin to allow the biomaterials produced to be applicable especially in medicine It is therefore an object of the present invention to provide such a method; such method should also be specifically suitable for medical purposes, especially for therapy and surgery.

Therefore, the present invention provides a method for the production of three-dimensional silk products, wherein native silk fibres are formed to a three-dimensional silk product and the silk product formed is subjected to a degumming step wherein a borate buffer is used as degumming agent and wherein the silk product formed is preferably contacted with an aqueous ethanol containing buffer prior to the degumming step.

The method according to the present invention allows efficient degumming of silk, especially degumming of three-dimensional products. Whereas degummed products according to the prior art still contain at least 1% (w/w) (or even at least 2% (w/w)) of sericin, the products according to the present invention are essentially free of sericin which means that the sericin content is below 0.1% (w/w), preferably below 0.05% (w/w), especially below 0.01% (w/w) (also depending, in practice, on the method for detecting sericin which have different detection limits). For example, for the presented products, no sericin residues are visible in electron microscopy or no sericin colouring visible in sericin staining assays. It is also clear that textile products (such as those disclosed by JP 2 269870 A or JP 1 229803 A) with a high sericin content are not suited for the medical field and therefore in principle excluded in the present invention (independent of the way sericin has been (partially) removed).

It was surprisingly found in the course of the present invention that sericin can be efficiently removed from complex three-dimensional silk products made of native silk fibres with the degumming step according to the present invention. This allows the production of a three-dimensional product with the natural silk fibre (with sericin still part of the fibre) which provides significant advantages and possibilities due to the better handling properties of natural silk fibres compared to degummed silk fibres or reprocessed silk fibres (from fibroin solutions).

In contrast to prior art methods, such as alkali or protease treatment for which no successful degumming was reported for silk fabrics (Fan et al., 2008, 2009; Freddi et al., 2003), the degumming method provided with the present invention enables the obtainment of three-dimensional silk products which are essentially free of sericin. Whereas prior art methods did not succeed to remove sericin from highly twisted weft yarns in e.g. fabrics and the like, the degumming method according to the present invention provides a sericin removal necessary for medical application.

With the present invention it is therefore possible to produce complex three-dimensional silk structures in advance and perform the degumming step afterwards. This allows the provision of more and robust complex silk structures than by employing degummed silk fibres or reprocessed silk fibres, which is a significant advantage in modern surgery. Also the production process as a whole is therefore more robust and suitable for industrial mass production, because it does not suffer from the weakened properties of the degummed fibres.

Within the present invention, "three-dimensional silk products" shall not only be understood as products having none of the three dimensions being irrelevant compared to the other two but as products that have more than one level of geometric hierarchy. Textile-engineered structures with more than one level of geometrical hierarchy according to the present invention are complex three-dimensional structures having a diameter in the smallest dimension ("thickness") of at least 0.5 mm. In fact, preferred three-dimensional products according to the present invention have a diameter in the smallest dimension of at least 1.0 mm, preferably of at least 2.0 mm, especially of at least 5.0 mm. Accordingly, the scaffold used within the present invention can be subdivided into a sheathing and a core part ($1^{st}$ hierarchical level). The core part itself can further be separated into 4 strands, where a single strand is built up of 8 bundles ($2^{nd}$ hierarchical level). One of this bundles can further be divided into 24 twisted yarns ($3^{rd}$ hierarchical level) each consisting of 6 single silk fibers ($4^{th}$ hierarchical level). This multi-filament graft has a diameter of 5.8 mm. In the present invention the removal of sericin from a three dimensional scaffold intended to be used as anterior cruciate ligament of high hierarchical order (i.e. at least two levels of geometric hierarchy) is shown. The degumming of this complex structure was not possible in the case of the common used sodium carbonate but with the borate buffer solution according to the present invention it could be achieved.

Moreover, a preferred three-dimensional silk product according to the present invention has a ratio of the three dimensions wherein the smallest dimension is not less than 1/100 of the largest dimension, preferably not less than 1/50 of the largest dimension, especially not less than 1/20 of the largest dimension. In preferred embodiments (e.g. for the anterior cruciate ligaments), the two smaller dimensions may even be in comparable ranges, e.g. have a ratio of 1:1 to 1:5 (see e.g. FIGS. 7 and 10).

In contrast to the scaffold used within the present invention silk structures that have been produced of raw silk fibers in advance and then underwent a degumming procedure are of simple structures, mainly plain meshes (see below).

The scaffold used in the study of Chen et al., 2008 consists of 12 warp-knitted yarns where one yarn is built up by one single silk fiber (one hierarchical level). Similarly, the meshes used in studies of Liu et al., 2008 and Fan et al., 2008 are made of yarns where each yarn consists of maximal 80 single silk fibers. Hence, these meshes show only one hierarchical level and therefore are rather loose fibrous structures which are highly accessible for degumming solutions. Moreover, these plain meshes are described to have an average thickness in the sericin-free state of about 0.325+/−0.116 mm, which is only 1/10 of the scaffold usually provided by the present invention for an anterior cruciate ligament as presented in the example section of the present invention. In the field of ligament and tendon tissue engineering with silk as biomaterial a lot of research has been done in the recent past (reviewed in: Vepari et al., Prog. Polym. Sci. 32 (2007), 991-1007). Taken together their loose fibrous structure and thickness values below 0.5 mm enables the degumming with common agents like sodium carbonate. These differences can also be seen from FIGS. 11 A and 11 B in comparison with e.g. FIG. 1, 7 or 10).

Efficiency of sericin removal by the process according to the present invention was shown by weight loss, picric acid and carmine staining and scanning electron microscopy. Furthermore, cell viability and proliferation of anterior cruciate ligament fibroblasts (ACLF) and adipose-derived stroma cells (ASC) in medium contact with silks were examined using MTT assay and BrdU-Elisa, respectively.

A "native silk fibre" according to the present invention is any natural silk fibre comprising sericin. A "native silk fibre" has intact fibroin structure. In contrast thereto, a "regenerated silk fibre" is a silk fibre which has been newly created from a fibroin solution/suspension by spinning processes or related artificial processes for creating artificial silk fibres. A native silk fibre can be taken from the cocoons and physically treated for obtaining the silk fibre (usually, the cocoons are dissolved in boiling water in order to obtain individual long fibres to be extracted and fed into a spinning reel; however, no chemical steps are applied onto a "native silk fibre" which affects the fibroin structure of the silk fibre obtained from the natural source).

Accordingly, any silk fibre from natural sources which comprise sericin can be subjected to the method according to the present invention. The major industrial source for such fibres is, of course, the mulberry silkworm *Bombyx mori*, however, silk fibres from other silkworms (Lepidopteron) can also be used in the process according to the present invention. Silkworms can generally be distinguished in mulberry (*Bombyx mori, Bombyx mandarina*) and non-mulberry (*Antheraea (A.) mylitta, A. proylei, A. pernyi, A. yamamai, A. frithi, A. assamensis, Samia ricini, A. atlas, Gonometa postica, Cricula trifenestrata*) silkworms. Pattern-similarity of amino acid composition of extracted sericin between wild silkworms and domesticated silkworms are at least 97%, which demonstrates the high number of conserved amino acid sequences among different species of silkworms (Mondal et al., Caspian J. Env. Sci. 5 (2007), 63-76). Sericin can be successfully removed from any native silk fibres independent from the silkworm species. Other possible natural silk sources are from other insects then silkworms such as ants, moths, fleas, sawflies, mantises etc.

Preferably, the degumming step is performed by contacting the silk product formed with a borate buffer comprising borate ions, especially sodium borate, boric acid and carbonate ions, especially sodium carbonate.

According to a preferred embodiment of the present invention, a purification step is performed before the degumming step with ethanol in an aqueous solution containing 1 to 98% (v/v) ethanol, preferably 60 to 80% (v/v) ethanol, especially 65 to 75% (v/v) ethanol.

Preferably, borate is used in the degumming step in an aqueous solution containing 10 to 2000 mM borate, preferably 50 to 1000 mM borate, especially 100 to 1000 mM borate. Preferably, the borate buffer has a pH of 7 to 11, preferably of 8 to 10, especially from 8.5 to 9.5. When defining the pH for a given set-up, care must be taken that the combination of pH, concentration of buffer components and temperature/duration are set which prevent substantial destruction of the fibroin structures in the product. Preferably, the ethanol purification step and the degumming step are carried out at elevated temperatures, preferably from 60 to 100° C., preferably from 80 to 100° C., especially from 90 to 100° C. Both, the ethanol purification step and the degumming step are preferably carried out for a time period of 30 min or more, preferably 60 min or more, especially 90 min or more. There is no technical upper limit for these treatments, from economical perspectives, durations of 48 h or more, 24 h or more, or even 10 h or more, are less preferred, since degumming is already completed before.

The present invention now allows all production steps for the creation of complex silk products which are possible for the natural silk fibre. The risk of fissuring and rupture of the silk fibre or the silk product is significantly decreased with the method according to the present invention.

Accordingly, all techniques known for building up three-dimensional structures with native silk fibres can be performed with the present invention. Preferably, formation of a three-dimensional silk product is performed by weaving, braiding, knitting or pressing.

It is possible to perform the method according to the present invention with any native silk fibre; however, the method has been specifically optimised for silk fibers from the *Bombyx mori* silkworm. This is also the major industrial source of native silk fibres for textile industry. However, also other sericin-containing silk fibres can be used for the production of the silk products according to the present invention.

Most preferred native silk fibres are those from *Bombyx mori* silkworm cocoon. Silk fibers from the *Bombyx mori* silkworm have a triangular cross section with rounded corners, 5-10 μm wide. The fibroin-heavy chain is composed mostly of beta-sheets, due to a 59-mer amino acid repeat sequence with some variations. The flat surfaces of the fibrils reflect light at many angles, giving silk a natural shine. The cross-section from other silkworms can vary in shape and diameter: crescent-like for Anaphe and elongated wedge for tussah. Silkworm fibers are naturally extruded from two silkworm glands as a pair of primary filaments (brin), which are stuck together, with sericin proteins that act like glue, to form a bave. Bave diameters for tussah silk can reach 65 μm.

As already stated above, any three-dimensional silk product may be processed according to the present invention. Preferably, products are made with the present method which are used in human and veterinary surgery (human surgery being preferred due to the possibility of providing pharmaceutically applicable silk products with the present invention), e.g. a medical implant, preferably a stent, a nerve conduit, a hernia meshwork, a ligature, especially an anterior cruciate ligament (ACL), or a cartilage and bone scaffolds.

On the other hand, the method according to the present invention can be used to produce cell culturing material, e.g. a cell culturing substratum upon which cells can be seeded for further growth or production of cellular components (e.g. recombinant proteins or other substances which are secreted out of the cells).

The method according to the present invention can easily be optimised depending on the very nature of the three-dimensional product or the nature of the native silk as well as on the specific degumming method.

According to a preferred embodiment, the method according to the present invention employs a degumming step which is carried out at a temperature of 20 and 100° C., preferably 70 to 100° C., especially at boiling temperature (e.g. around 100° C.)

The method according to the present invention can also be used for the production of two-dimensional silk products. In comparison to prior art methods for the production of two-dimensional silk product (Freddi et al., 2003), the present invention provides a superior method for the degumming of native two-dimensional silk structures made of native silk fibres. Therefore, the present invention provides also a method for the production of two-dimensional silk products, wherein native silk fibres are formed to a two-dimensional silk product and the silk product formed is subjected to a degumming step wherein the silk product formed is preferably contacted first with an aqueous ethanol buffer and subsequently subjected to a degumming step according to the present invention wherein a borate buffer is used as degumming agent.

Another aspect of the present invention relates to a three-dimensional silk product, obtainable by a method according to the present invention. The product obtainable according to the present invention has excellent mechanical stabilities, is biocompatible, especially free of adverse reactions due to sericin, is biodegradable and has an enormous morphologic flexibility. In contrast to other degumming methods, the present invention leads to products where the mechanical properties of the final product are not decreased to that extent, quite in contrast, the mechanical stabilities (e.g. tensile strength, etc.) are comparable to those of the native silk product and not decreased like in an alkali degummed product.

The three-dimensional silk product according to the present invention can be a matrix scaffold, preferably for medical use, especially for cell attachment, spreading, growth and differentiation. Preferred products according to the present invention are medical implants, preferably a stent, a nerve conduit, a hernia meshwork, or a ligature, especially an anterior cruciate ligament (ACL). Handling the production for such products is significantly advantageous according to the present invention, because the product is formed while sericin is still present on the silk fibre.

The products according to the present invention significantly differ from the products according to the prior art, since the present products are real three-dimensional products which are not made up from degummed one- or two-dimensional products brought into a certain shape by mechanistic handling. Therefore, the present products have also an inner structure which significantly differs from e.g. the products of e.g. Fan et al. 2008 or 2009.

The present invention also refers to a two-dimensional silk product, obtainable by a method according to the present invention.

Preferably, this product is a product in sheet form, preferably for medical use, especially a film, a membrane, a woven sheet or a mesh for cell attachment, spreading, growth and differentiation.

The present invention is further illustrated by way of the following examples and the drawings, yet without to be limited thereto.

Figure 3:
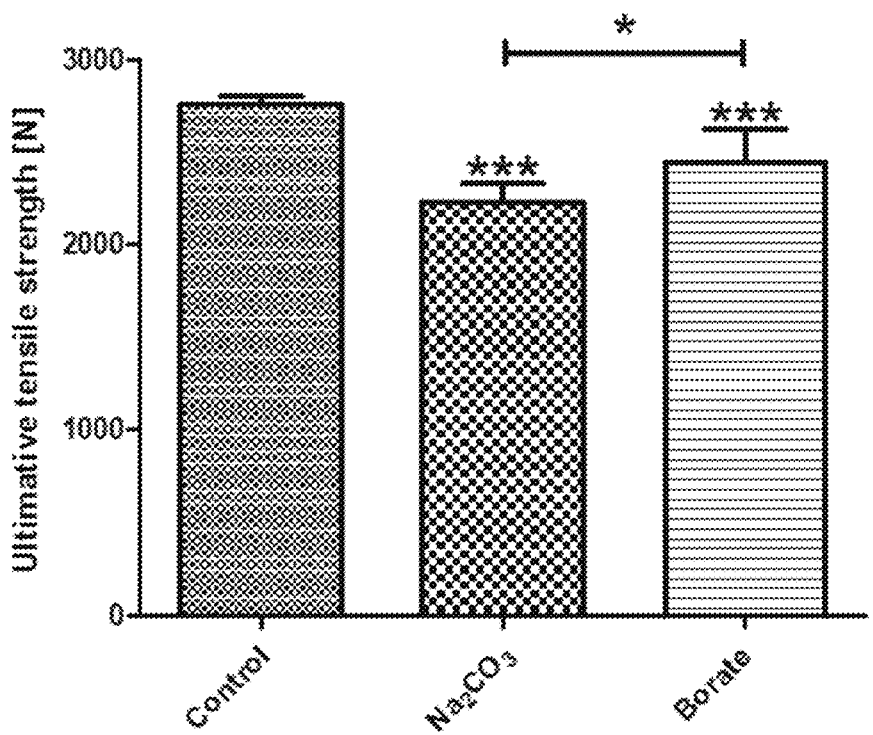

FIG. 3 shows UTS values of differently degummed silk scaffolds of wire-rope design. Undegummed silk scaffolds served as control. Silk scaffolds were degummed with alkaline solutions based on borate buffer or sodium carbonate ($Na_2CO_3$). Column heights correspond to the means of at least 7 values, error bars to the SD. *** indicates significant differences to control group, * indicates a significant difference of $P<0.05$.

Figure 4:
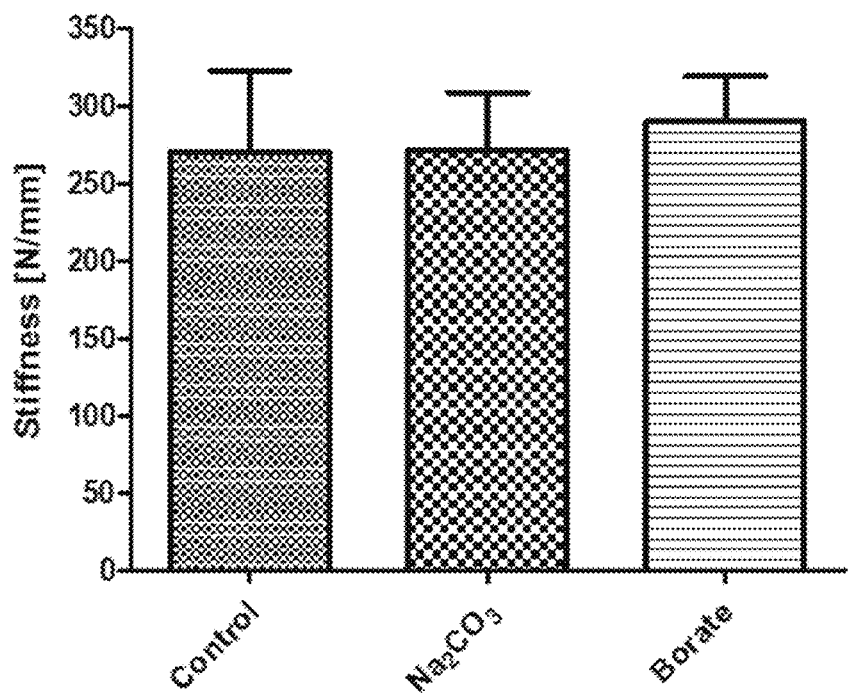

FIG. 4 shows stiffness values of differently degummed silk scaffolds of wire-rope design. Undegummed silk scaffolds serve as control. Silk scaffolds were either degummed with alkaline solutions based on borate buffer or with sodium carbonate ($Na_2CO_3$). Column heights correspond to the means of at least 7 values and the error bars to the SD.

Figure 5:
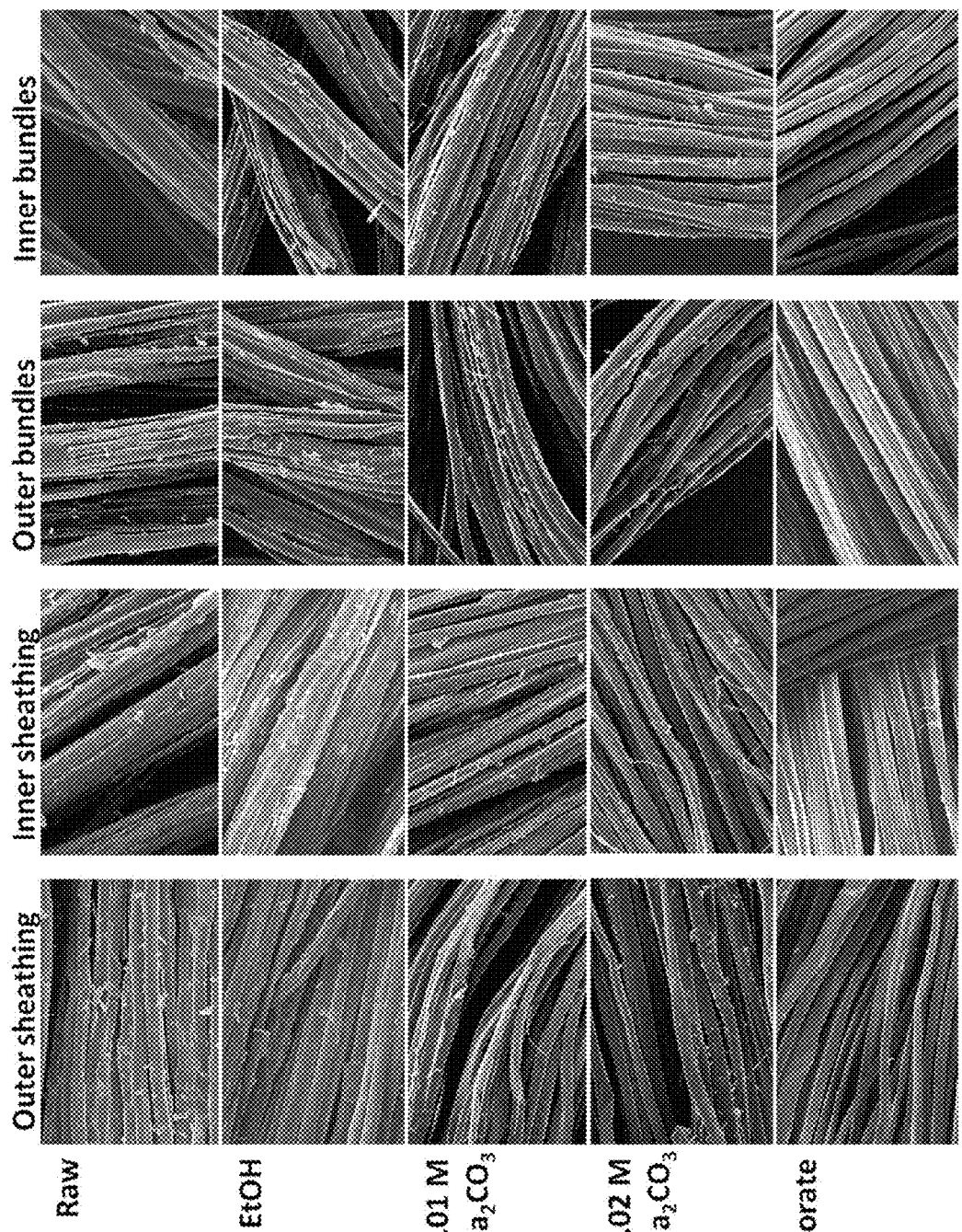

FIG. 5 shows scanning electron micrographs of differently degummed silk scaffolds. Raw) Non treated, raw silk fibers in their native state. EtOH) ethanol treated silk; 0.01 M $Na_2CO_3$) $Na_2CO_3$ degummed silk, using a 1.1 g/L sodium carbonate solution; 0.02 M $Na_2CO_3$) $Na_2CO_3$ degummed silk, using 2.1 g/L sodium carbonate solution; and borate) borate buffer degummed silk, using 0.2 M boric acid in a 0.05 M sodium borate buffer at pH=9.0 selected from different hierarchical origin; outer sheathing fibers, inner sheathing fibers, outer bundle fibers and inner bundle fibers. All images were obtained with a magnification of 500×.

Figure 6:
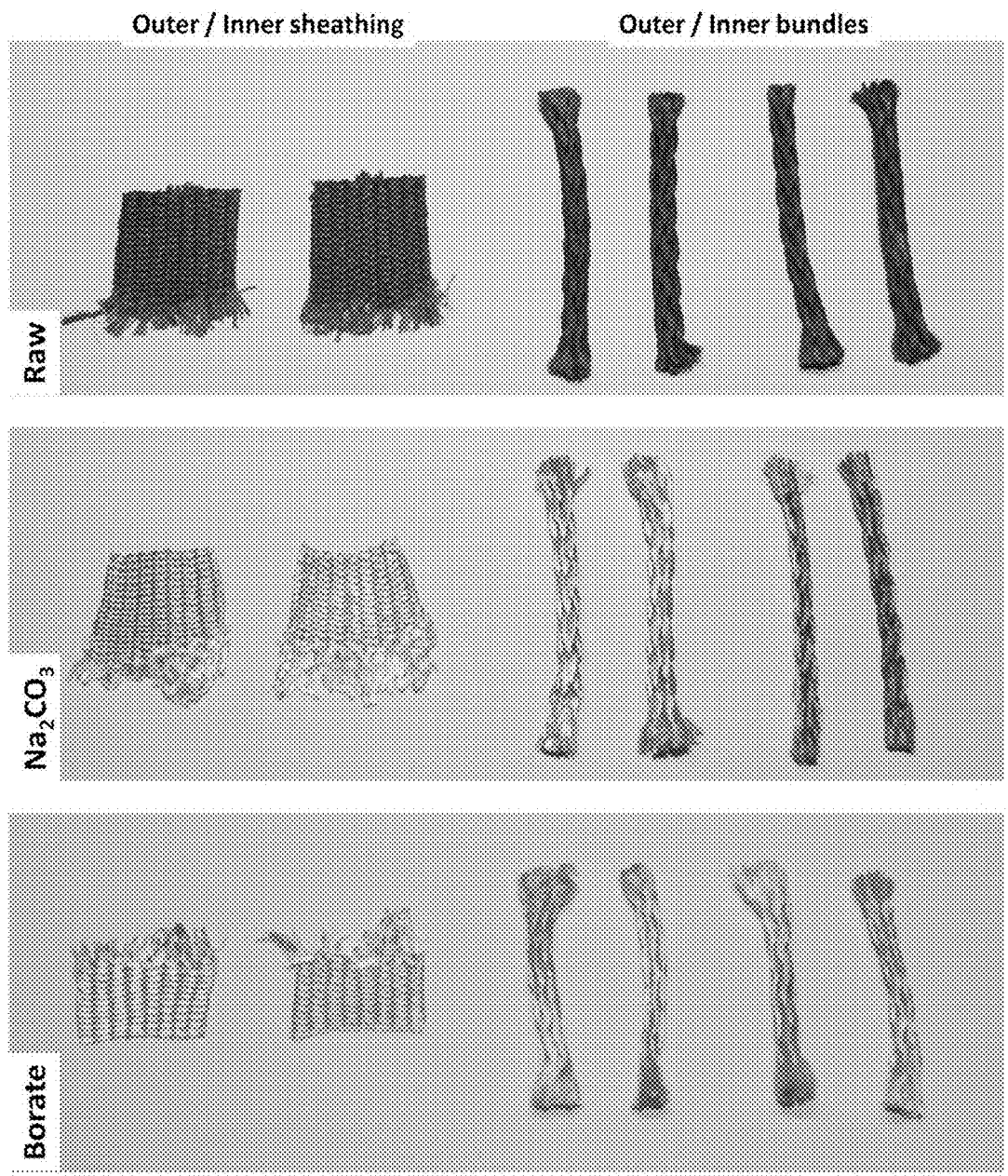

FIG. 6 shows picric acid and carmine staining of raw) undegummed raw silk scaffold, $Na_2CO_3$) sodium carbonate degummed silk scaffold and Borate) borate buffer degummed silk scaffold. In each picture from left to right: outside of the sheathing, inside of the sheathing, bundles facing the outside and the inside of the scaffold construct.

Figure 7:
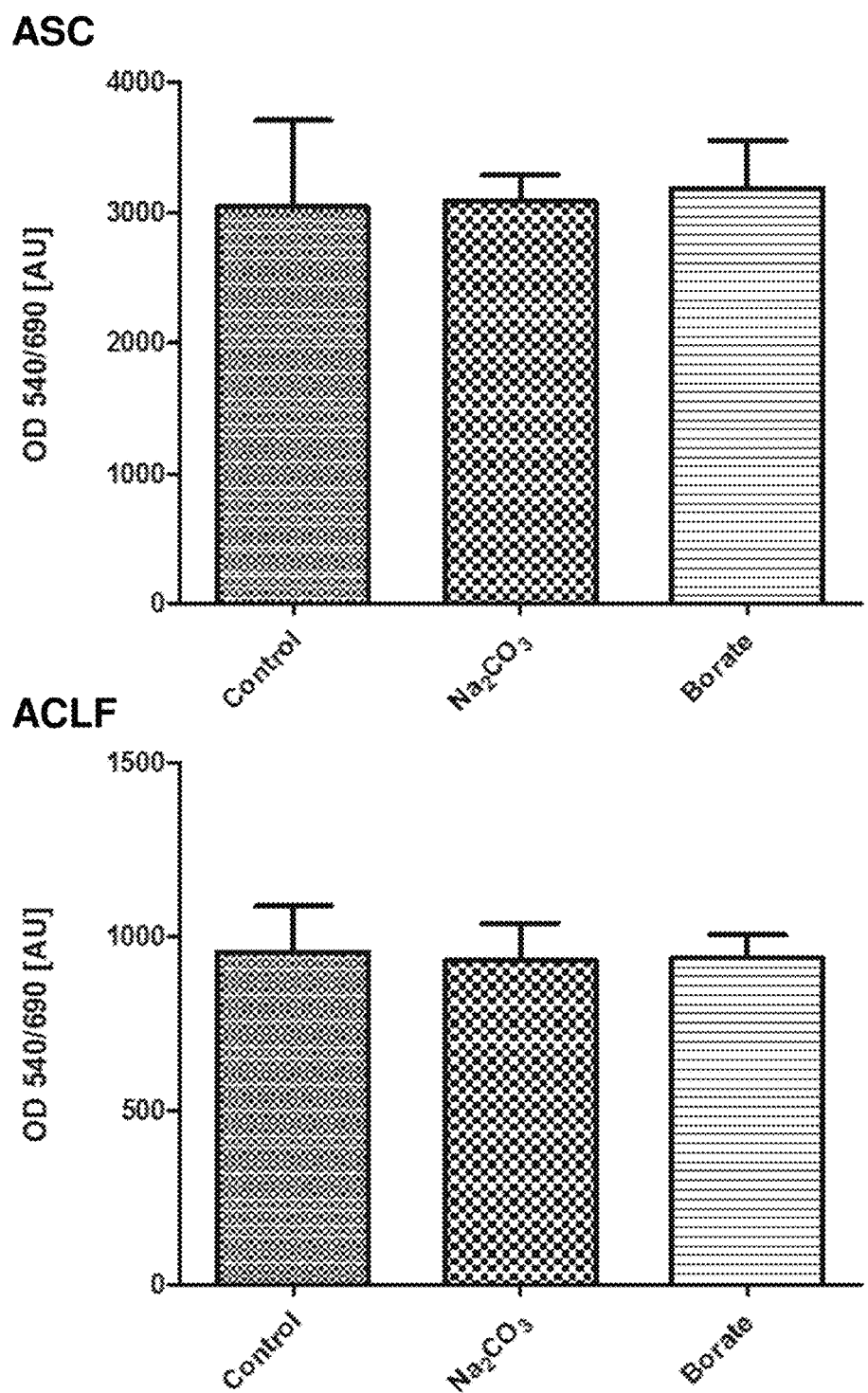

FIG. 7 shows MTT analysis of anterior cruciate ligament fibroblasts (ACLF) and adipose-derived stroma cells (ASC) cultured with different extraction media. Control, $Na_2CO_3$ and borate buffer corresponds to media that have been used to immerse differently treated silk scaffolds for 24 h in a humidified incubator at 37° C. in 5% $CO_2$, respectively. All data are means of 8 independent experiments±SD.

Figure 8:
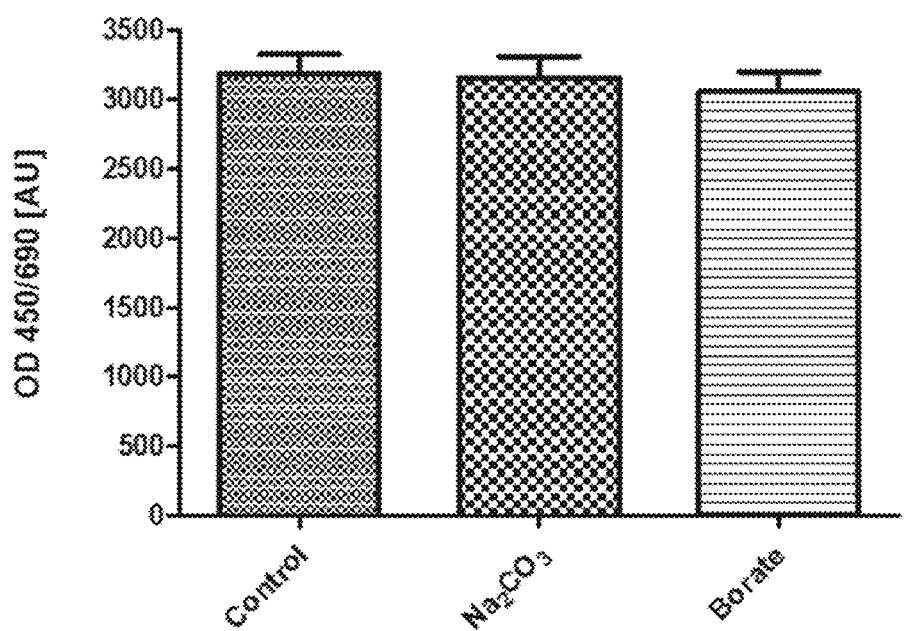
Figure 8:
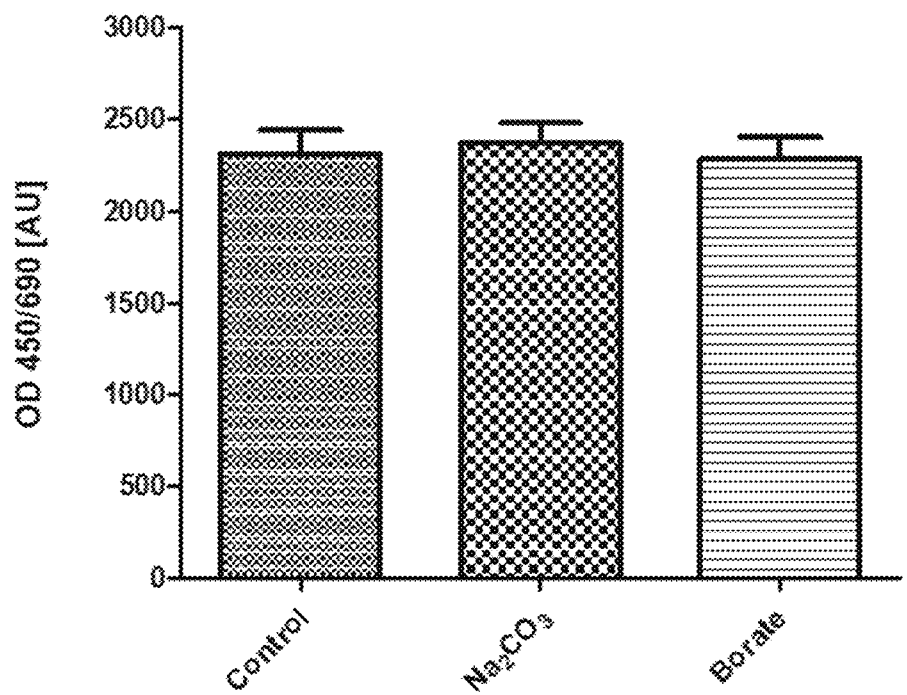
Figure 9:
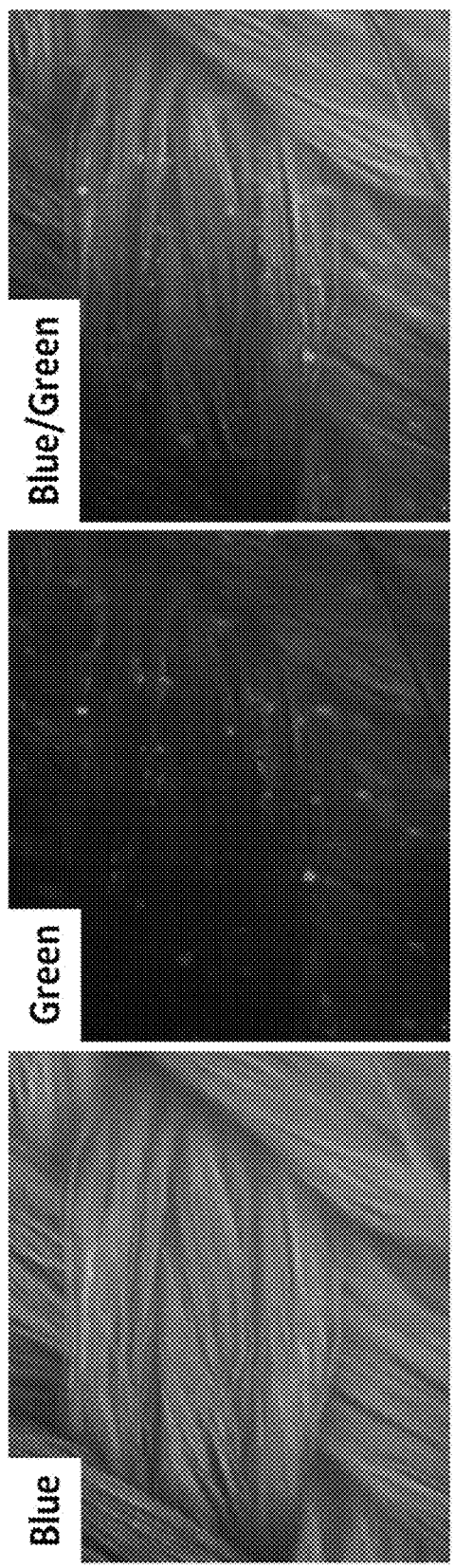

FIG. 8 shows BrdU analysis of anterior cruciate ligament fibroblasts (ACLF) and adipose-derived stroma cells (ASC) cultured with different extraction media. Control, $Na_2CO_3$ and borate buffer correspond to media that have been used to immerse differently treated silk scaffolds for 24 h in a humidified incubator at 37° C. in 5% $CO_2$, respectively. All data are means of 8 independent experiments±SD FIG. 9 shows viability of adipose-derived stroma cells (ASC) on borate buffer degummed inner fiber bundles visualized by live-cell staining using CalceinAM (Green). Blue) is a fluorescence image of the blue channel showing autofluorescence of the silk fibroin fibers. Blue/Green indicates an overlay of the autofluorescence picture of silk (Blue) on the Calcein AM-stained cells (Green).

Figure 10:
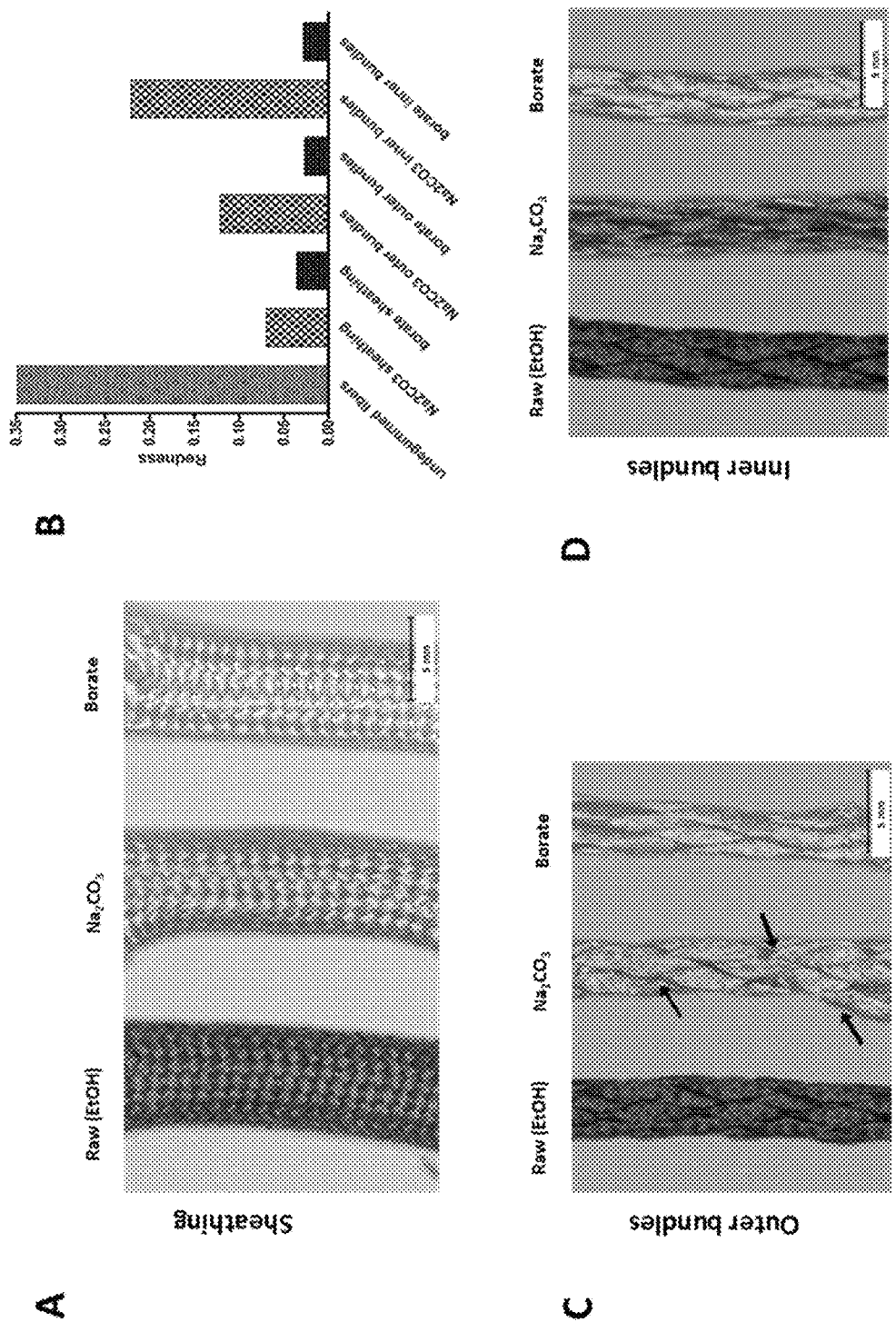

FIG. 10 shows sericin removal determined via picric acid and carmine staining (A-D). Picric acid and carmine staining of undegummed raw silk scaffold (Raw), sodium carbonate degummed silk scaffold ($Na_2CO_3$) and borate buffer degummed silk scaffold (borate) of sheathing, bundles facing the outside and the inside of the scaffold construct. B) shows the absolute values of "redness" calculated from the RGB-values of the images using Definiens XD 1.0 software. redness=(2×red−green−blue)/(2×red+green+blue). Scale bars indicate 5 mm.

Figure 11A:
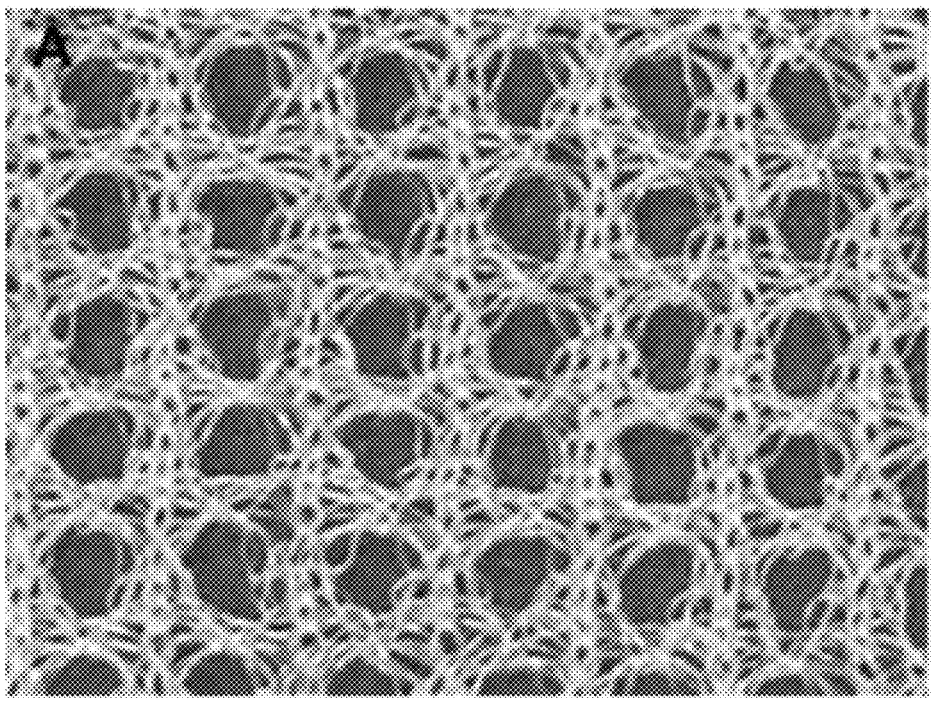
Figure 11B:
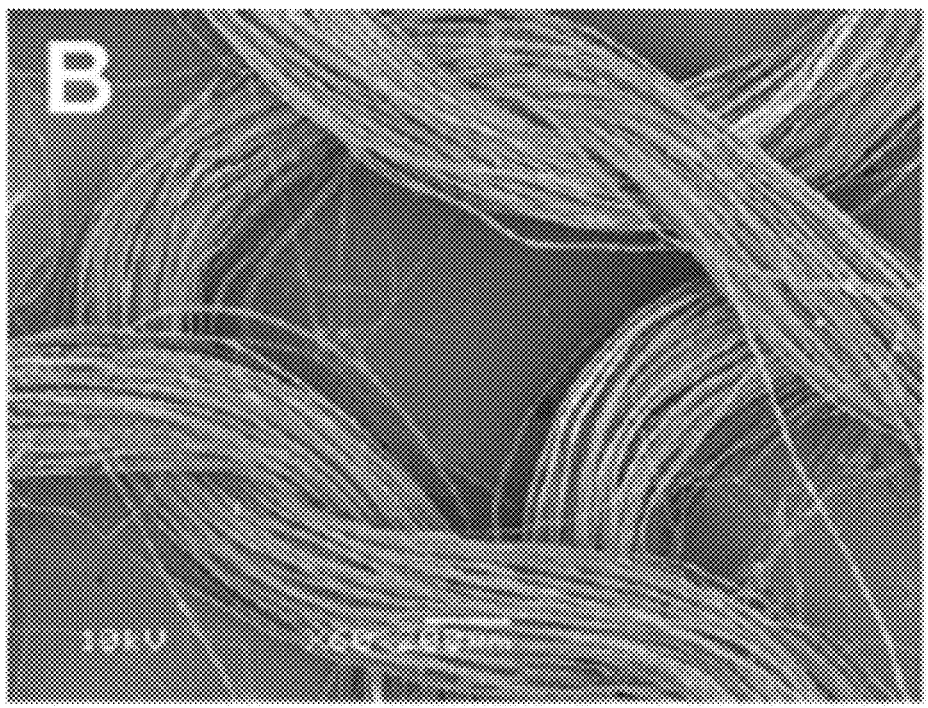

FIG. 11 shows silk meshes with only one level of geometrical hierarchy as disclosed in Chen et al., 2008 (11A; SEM image of the knitted silk scaffold; the pore size was approximately 1×1 mm) and Liu et al., 2008 (11B; SEM image of the knitted silk scaffold, scalebar=200 µm).

EXAMPLES

Materials and Methods
Materials

If not indicated otherwise, all reagents were purchased from Sigma (Vienna, Austria) and were of analytical grade.
Silk-Matrix Design White raw *Bombyx mori* silkworm fibres of 20/22 den, 250 T/m, were purchased from Testex AG (Zürich, Switzerland). Braided scaffolds were then produced in cooperation with Edelrid (Edelrid GmbH, Isny im Allgäu, Germany). The braided scaffold exhibits a wire-rope design and can be subdivided into a sheath and a core component. Both sheathing and core elements have a hierarchical structure composed of strands, bundles, twisted yarns and single silk fibres (see FIG. 1). The basic unit of the braiding structures represents a twisted yarn that is formed by six single silk fibers. Six and twenty-four twisted yarns are the structural basis for sheathing and a strand, respectively. The entire scaffolds consists of the core component (four strands) enveloped by the tubular sheathing, resulting in a total diameter of 5.8 mm. The tubular structure of the sheath and the core strands are made with the help of a commercial braiding machine with fibres in each of sixteen bobbins. The braiding density of the sheathings and the core bundles totals 10 and 25 crossings/French inch, respectively. One French inch corresponds to 27.072 mm.
Purification Step with Ethanol In order to clean the scaffolds made of raw *Bombyx mori* silk from substances originating from the preparation process such as sizing agents or inherent substances on raw silk such as waxes a washing step with 70% Ethanol was performed. Therefore the scaffolds have been immersed in 70% Ethanol in a round bottom flask and cooked under reflux for 2 times, batchwise.
Degumming Two different degumming solutions were used throughout the study to prepare samples for analysis; (i) 0.02 M $Na_2CO_3$ and (ii) 0.2 M boric acid in a 0.05 M sodium borate buffer at pH=9.0 (Jiang et al., 2006). For scanning electron microscopy analysis one group of samples was degummed with 0.01 M $Na_2CO_3$. The degumming method proceeded as follows: 8 cm long scaffolds were placed in a 1000 ml beaker, 500 ml degumming solution was added, the beaker was sealed with aluminum foil and heated on a common magnetic stirrer including a hot plate until degumming solutions started to boil. After 45 min the degumming solution was renewed and the boiling step repeated. After degumming, samples were thoroughly washed in $ddH_2O$. Finally, all samples were air-dried before further testing took place.
Weight Loss The efficiency of each degumming method was quantitatively assessed by measuring a loss in weight. Weight loss is expressed as a percentage of the initial weight and the weights were recorded until successive weightings agreed within 0.1 mg.

Sampling of Silk Fibers

Figure 1:
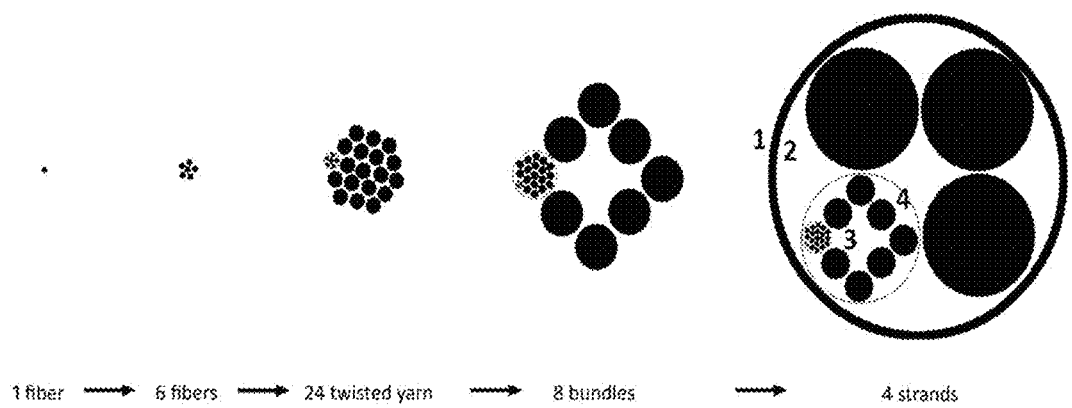
FIG. 1 shows the schematic of the silk scaffold hierarchy. Numbers indicate the sampling location of silk fibers for further analysis: 1) outer sheathing, 2) inner sheathing, 3) outer bundle and 4) inner bundle fibers.
Figure 2:
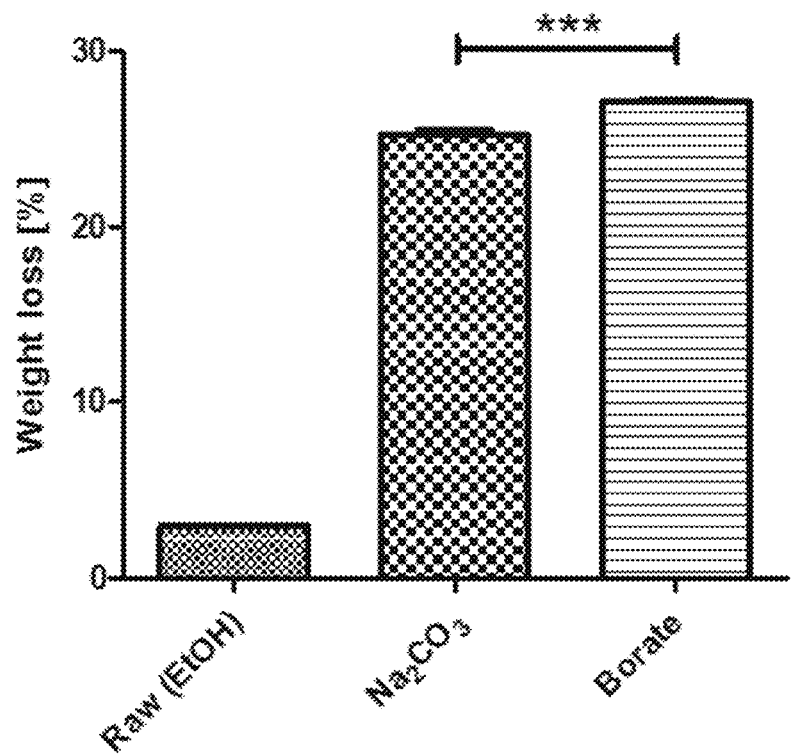
FIG. 2 shows the weight loss of silk scaffolds as a consequence of A: silk samples boiled in 70% Ethanol, B: silk samples boiled in 70% Ethanol and $Na_2CO_3$ degumming performed and C: silk samples boiled in 70% Ethanol and borate buffer degumming performed. All data are means of 8 independent experiments±SD, *** indicates a significant difference with $P<0.001$.

Using picrocarmine staining and SEM-analysis the location-dependent degumming efficiency was verified. Silk fibers from different locations within the wire-rope designed scaffold were sampled (FIG. 1).
Picrocarmine Staining Picrocarmine staining is a classical staining method for tissue sections and is performed by mixing solutions of carmine and picric acid. According to a method described by Wang et al. (Wang et al., 2011) this staining was used as a qualitative evaluation method of the silk degumming effect. In brief, a staining solution is made by mixing carmine dissolved in 25% ammonia with saturated picric acid aqueous solution and adjusting the pH to 8.0-9.0. To stain the silk fibers, matrices are immersed within the staining solution in separated test tubes and are then heated in a boiling water bath for 5 min. Subsequently the samples were thoroughly washed with $ddH_2O$ and dried at room temperature. Digital images of stained silk matrices were obtained using a digital camera (Ixus 100S, Canon, Japan). These images have then been used to calculate respective "redness" values using Definiens XD 1.0 software (Definiens AG, Germany, Munich) based on the following calculation formula: Redness=(2×red−green−blue)/(2×red+green+blue).
Scanning Electron Microscopy (SEM) Analysis After the degumming process, the scaffolds were immediately rinsed with phosphate buffered saline (pH 7.4) and fixed in 2.5% glutaraldehyd o/n at room temperature. Samples were then dehydrated through graded ethanols followed by hexamethyldisilazane, and allowed to air dry in a fume hood. The samples were sputter coated with Pd—Au using a Polaron SC7620 sputter coater (Quorum Technologies Ltd. East Grinstead, United Kingdom), and examined using a JEOL JSM-6510 scanning electron microscope (JEOL GmbH, Eching/Munich, Germany) at 3 kV.
Mechanical Testing The silk scaffolds underwent tension testing using a Zwick Z050 material testing machine (Zwick GmbH & Co. KG, Ulm, Germany). To guarantee stable fixation within the testing machine, the scaffolds ends were embedded in epoxy resin (epoxy resin BK, VOSSCHEMIE GmbH, Uetersen, Germany). Prior to testing, scaffolds were incubated in PBS for at least 24 h. Samples were pulled to failure at a strain rate of 10 mm/min at 23±2° C. and a relative humidity of 45-65%. Pull-to-failure tests were performed with 50 N of pretension. The highest load attained before failure was taken as the ultimate tensile stress (UTS). To calculate stiffness values, the linear portion of the stress/strain curve was used.
Cell Culture
Anterior Cruciate Ligament Fibroblasts (ACLF)

The ethical review board of the AUVA (IRB) approved the procedure of collecting ACL tissue from patients undergoing total ACL reconstruction. Anterior cruciate ligament fibroblasts (ACLFs) were obtained by a modified method based on a protocol of Nagineni et al. (Nagineni, Amiel, Green, Berchuck, & Akeson, 1992). In brief, ACL tissue was harvested and minced aseptically into small pieces of 1-3 $mm^3$. Then, these explants were transferred into 100 mm cell culture petri dishes and cultured in DMEM containing 10% FCS (PAA, Pasching, Austria), 2 mM L-glutamine, 100 U/mL penicillin and 0.1 mg/mL streptomycin. Cell outgrowth from the explants was monitored until 90% confluency was reached, followed by subcultivation of the cells.
Adipose-Derived Stroma Cells (ASC)

Subcutaneous adipose tissue was obtained during outpatient liposuction procedures under local tumescence anesthesia (IRB consent obtained). As previously described (Wolbank et al., 2007) adipose derived stromal cells (ASC) were isolated and cultured in a medium containing DMEM-low glucose/HAM's F-12 supplemented with 10% FCS (PAA, Pasching, Austria), 2 mM L-glutamine, and 1 ng/mL recombinant human basic fibroblast growth factor (rhFGF, R&D Systems, Minneapolis, USA)

Cell Viability and Proliferation Testing

To test the influence of differently degummed silk scaffolds on cell viability and proliferation behavior, 1 g of degummed silk was immersed in 5 ml cell culture-medium for at least 24 h at 37° C. in a 5% $CO_2$ environment. In parallel, cells were seeded into 24-well plates with a cell density of $0.2 \times 10^5$ cells/well. Then respectively the medium containing leach-out products from the silk material was filtered (0.22 μm, Rotilabo, Karlsruhe, Germany) and used to exchange the media in the cell cultures. As a negative control, standard culture medium was used.

Proliferation

Proliferation was determined using a 5-bromo-2-deoxyuridine (BrdU) uptake assay (Cell Proliferation ELISA assay Kit, Cat 1647229, Roche Diagnostics) according to the manufacturer's instructions. Briefly, cells were cultured with the respective media containing 100 μM BrdU for 12 h in a humidified incubator at 37° C. and 5% $CO_2$. Media was removed and the culture plates were air-dried for 15 min. FixDenat® solution was added for 30 min and subsequently incubated with anti-BrdU POD (peroxidase) antibodies for 60 min at room temperature. The plate was washed three times with PBS and tetramethyl benzidine was added for 30 min as a substrate. The reaction was stopped by adding 1 M $H_2SO_4$ and absorption was measured at 450 nm with 690 nm as a reference wavelength.

Cell Viability/Cytotoxicity Testing by MTT Assay

Cell culture medium was aspirated and the respective cell culture medium containing 650 mg/ml MTT [3-(4,5-dimethylthiazol-2-yl)-2,5-diphenyltetrazolium]bromide was added to each well. Cells were incubated for 1 h at 37° C. in a 5% $CO_2$ environment. Medium was aspirated and MTT formazan precipitate was dissolved in DMSO by shaking it mechanically in dark for 20 min. Aliquots of 100 μl of each sample were transferred to 96-well plates. Light absorbance at 550 nm was read immediately on an automatic microplate reader (Spectra Thermo, TECAN Austria GmbH, Austria). Optical density (OD) values were corrected for an unspecific background.

Cell Viability on Borate Buffer Degummed Silk Scaffold

To visualize cell viability of ASCs on borate buffer degummed silk scaffolds, an inner fiber bundle of the whole construct with 1 cm in length was seeded with a $1 \times 10^6$ cells/mL cell suspension for 24 h at 37° C. in a 5% $CO_2$ environment. The cell-seeded scaffold materials were then stained with Calcein-Acetoxy-methylesther (CalceinAM, Invitrogen, Lofer, Austria). Therefore, the constructs were incubated for 15 min in CM containing 5 mg/ml CalceinAM, and washed with PBS. After washing with PBS again, microscopic fluorescence pictures were taken employing a Leica DMI6000B epifluorescence microscope (Leica Microsystems GmbH, Wetzlar, Germany).

Statistical Analysis

All calculations were performed using GraphPad software (GraphPad software, Inc., La Jolla, Calif., USA). Normal distribution of data was tested with the Kolmogorov-Smirnov test. One-way ANOVA followed by Tukey's post hoc test was used to conduct statistical significance and P-values below 0.05 were considered statistically significant.

Results:

Weight Loss

To confirm the effectiveness of borate buffer based degumming compared to the classical $Na_2CO_3$ degumming method, the weight loss of treated silk scaffolds was determined. Prior to sericin removal, the silk scaffolds were boiled in 70% Ethanol (w/w) to detach any possible textile preservatives. This treatment with alcohol led to a silk scaffold weight loss of 2.9%±0.1%. The following degumming process with $Na_2CO_3$ or borate buffer respectively resulted in a weight loss of 25.2±0.3% and 27.1%±0.1%.

Influence of Degumming on the Mechanical Properties of Wire-Rope Silk Scaffolds

The tensile parameters obtained from pull-to-failure testing are summarized in table 1. Supplementary, the table also contains reference values, linear stiffness (242±28 N/mm) and UTS (2160±157 N) of a human femur-ACL-tibia complex from a study of Woo et al. (Woo, Hollis, Adams, Lyon, & Takai, 1991).

TABLE 1

Influence of the degumming process on mechanical properties of a wire-rope silk scaffold and reference values of a human ACL taken from Woo et al. (Woo et al., 1991), All data are means of at least 7 independent experiments ± SEM.

| Silk matrix | UTS [N] | Stiffness [N/mm] |
|---|---|---|
| Native, undegummed | 2757 ± 42 | 270 ± 49 |
| $Na_2CO_3$ degummed | 2230 ± 94 | 271 ± 34 |
| Borate buffer degummed | 2440 ± 182 | 290 ± 29 |
| Native ACL | 2160 ± 157 | 242 ± 28 |

Ultimative Tensile Strength (UTS)

Both employed degumming methods cause a significant decrease in UTS values compared to the undegummed control (FIG. 3). Raw undegummed silk scaffolds, borate buffer degummed silk scaffolds and sodium carbonate degummed scaffolds showed UTS values of 2757±42, 2440±182 and 2230±94, respectively. These values correspond to 89% of the initial UTS prior to the removal of sericin for the borate buffer degummed silk scaffolds and to 81% for the sodium carbonate degummed scaffolds. Thus, the UTS for borate buffer degummed scaffolds are significant higher than those obtained with classical sodium carbonate degumming.

Stiffness

Stiffness of silk scaffolds either degummed with sodium carbonate or with borate buffer are quite equivalent, ranging from 271±34 N/mm and 290±29 N/mm, respectively, and are not statistically different from undegummed native silk scaffolds (270±49).

SEM-Analysis

To investigate the efficiency of sericin removal dependent on 3D architecture, fibers of different hierarchical origin have been collected and visually analyzed using SEM. FIG. 5 shows the surface morphology of these silk fibers. Obviously, undegummed raw SF fibers exhibit a nonuniform, gum-like coating of sericin covering the underlying silk fibroin filaments (FIG. 5 Raw). The silk fibers in FIG. 5, row "EtOH" have been boiled in ethanol to get rid of lipoid substances, such as textile-engineering preservatives. Row 2 represents undegummed raw SF fibers which have been treated with alcohol. Apparently, there is no difference between the alcohol treated and the untreated SF fibers. The micrographs of SF scaffolds degummed by the classical $Na_2CO_3$ methods (FIG. 5 0.01 M $Na_2CO_3$, 0.02 M $Na_2CO_3$) and by the borate buffer based method (FIG. 5 Borate) show differences in the sericin removal, especially in inner parts of the 3D structured scaffold. Borate buffer degummed scaffolds (FIG. 5, Borate) exhibit sericin-free SF fibers, consistently from the outer sheathing to the inner fibers.

Picric Acid and Carmine Staining

Apart from SEM analysis, sericin removal was also confirmed by picric acid and carmine staining. As described in Wang et al. (Wang et al., 2011) fibroin and sericin adsorb carmine and picric acid differently. Sericin absorbs both carmine and picric acid simultaneously whereas fibroin selectively adsorbs picric acid molecules. Therefore, a red coloration of silk can be attributed to residuals of sericin. FIG. 3A shows undegummed raw silk scaffolds stained intensively red, revealing the existence of substantial amounts of sericin on the surface of these scaffold fibers. FIGS. 3B and 3C represent the stained silk scaffolds degummed with $Na_2CO_3$ and borate buffer, respectively. $Na_2CO_3$ degummed silk scaffold display a sparse red color on the sheathing and on the outer fiber bundles but an intensified red color on inner bundle fibers. In contrast, silk scaffolds degummed with borate buffer exhibit a white to yellow color indicating successful removal of sericin, noticeable in the inner parts of the 3D hierarchical structured scaffold.

For densitometric analysis the different colored scaffolds have been photographed and the resulting pictures (FIG. 10A, C, E) have been used to calculate redness values from the different scaffold samples. In FIG. 10 B these values are displayed in a bar graph quantitatively demonstrating the observations described above.

Cell-Viability

MTT assay results for ACLF and ASC cells cultured in leach-out medium of differently degummed silk scaffolds are presented in FIG. 7. In both cell types, cell viability did not significantly differ from untreated, standard cell culture medium viability after 24 h of culture.

Proliferation

According to the results of the BrdU ELISA, no significant differences in cell proliferation were detected for either ACLF or ASC (FIG. 8) cells cultured in differently degummed silk extract fluids or untreated standard culture medium after 24 h of culture.

Seeding of Cells on Borate Buffer Degummed Silk Scaffold

To verify cell viability of ASCs on borate buffer degummed silk constructs, a live-cell staining with CalceinAM was performed on an inner fiber bundles seeded with ASCs. FIG. 9 (Green) shows viable cells on the silk fibroin fibers. An overlay of the images from the blue channel (FIG. 9 Blue) on the green channel (FIG. 9 Green) demonstrates the attachment of the ASCs along the fiber structured scaffold material (FIG. 9 Blue/Green).

Discussion

In order to use scaffolds of silk fibers in TE and regenerative medicine applications, sericin removal is essential to guarantee biocompatibility. However, no study investigated the removal of sericin from silk scaffolds of a high hierarchical order. Therefore, the ability to degum prefabricated silk scaffolds, exhibiting several levels of geometric hierarchy with classical $Na_2CO_3$-solutions was investigated in comparison to a degumming method based on borate buffer. The standard procedure in TE is to remove the gum from raw silk prior to scaffold fabrication. However, the removal of sericin causes the silk fiber to fray and weakens its structural property, making it very difficult to textile engineer (e.g. knit or braid) them into scaffolds for TE applications. A labor intensive method to enhance the processing characteristics of sericin-free fibers was proposed by Liu et al. (Liu et al., 2007). In this study sericin is replaced by chemical cross-linking sericin-free silk fibers with gelatin, which serves as a sliding surface and guarantees textile-engineering processability. In other studies silk scaffolds have been fabricated in advance and a degumming process was performed afterwards (Fan et al., 2009)(Fan et al., 2008)(Chen et al., 2008). Nevertheless, the structural bases of all of these studies were plain meshes. Compared to high order hierarchical textile engineered structures, they are easily penetrated by degumming reagents.

It is well known that the sericin content in *Bombyx mori* raw silk accounts for about 25 wt. %. Weight loss measurements indicated a more efficient removal of sericin using borate buffer based degumming solutions (27.1%±0.1% weight loss) versus the commonly used $Na_2CO_3$ degumming method (25.2±0.3% weight loss). These results are further supported by SEM analysis demonstrating $Na_2CO_3$ degummed silks still exhibits sericin residues, mainly located at the inner structures of the hierarchical scaffold. In contrast the surface of borate buffer, degummed silk scaffolds was very smooth and clean, independent of sampling location. Picric acid and carmine staining substantiated the results of the SEM analysis by presenting sericin residues as red colored areas in the $Na_2CO_3$ treated silks, especially on fibers of the inner structure. Results obtained by weight loss measurements, SEM analysis and PACS staining demonstrated effective sericin removal with borate buffer based degumming.

To analyze the effect of degumming on the mechanical properties of silk structures, pull-to-failure tests with degummed and undegummed silk scaffolds of wire-rope design were performed. The decrease in mechanical strength of silks (UTS) after degumming is consistent with previous literature (Liu et al., 2007)(Wang et al., 2011). Interestingly, UTS values were significantly higher in the borate buffer compared to the sodium carbonate degumming group. These results are in accordance with the findings of a study by Jiang et al. (Jiang et al., 2006). In that work the tensile parameters of differently degummed single silk fibers were determined with the result that borate buffer is the superior degumming reagent compared to sodium carbonate in preserving the inherent mechanical properties of silk fibers.

Single silk fibers exhibit lower elastic properties after sericin removal. Surprisingly, in the present invention the stiffness values did not significantly differ between degummed or non-degummed silk scaffolds. These results are inconsistent with the initial expectation that scaffold stiffness after degumming would decrease. A possible explanation for these converse findings might be that the majority of stiffness properties of a textile engineered scaffold are attributed rather to its hierarchical architecture than to the mechanical characteristics of single fibers. This explanation is supported by a study (Horan et al., 2006) in which the potency to tune UTS and stiffness of fabricated silk scaffolds by choosing various textile methods was demonstrated.

To gain insight into the in vitro biocompatibility differences between differently degummed silk scaffolds in combination with adipose derived stroma cells (ASC) and anterior cruciate ligament fibroblasts (ACLF) cells, (both cell types are intended to be used in future ligament TE approaches) cell viability and proliferation assays were carried out. In both assays, it was tested whether silk fibroin extract fluid had negative effects on cell viability and cell proliferation. MTT assay results suggested that, regardless of the used degumming solution, fluid extracts of silks have no cytotoxic effects on the investigated cell types. Analysis of cell proliferation by means of BrdU incorporation revealed no alterations in both degumming groups. Furthermore cell-viability of ASCs on borate buffer degummed silk was demonstrated via Calcein AM staining.

Despite promising in vitro results, further in vivo tests have to be carried out to investigate the effects of borate buffer degumming on in vivo behavior, especially regarding degradation rate.

CONCLUSION

These results show that the degumming of highly ordered hierarchical 3D scaffolds which is not possible with classic sodium carbonate degumming solutions can be achieved via a borate buffer based system, preferably together with an ethanol washing step. While substantially preserving the mechanical integrity of silk scaffolds, borate buffer was found to be suitable for entirely removing the immune response-eliciting sericin, even in inner structures of the tested silk scaffold. The possibility to remove sericin well after the textile engineering process eases the production of highly ordered scaffold structures. This finding may foster the use of silk as scaffold material in further TE and regenerative medicine applications, which are in need of sophisticated and complex hierarchical structures.

The invention claimed is:

1. Method for the production of a degummed three-dimensional silk medical implant products, wherein native silk fibres are formed to a three-dimensional silk product and the silk product formed is subjected for at least 30 min to a degumming step wherein a borate buffer is used as degumming agent and wherein the silk product formed is contacted with an aqueous ethanol buffer prior to the degumming step wherein a borate buffer is used as degumming agent and wherein the three-dimensional silk product formed is contacted with an aqueous ethanol buffer prior to the degumming step, thereby obtaining a degummed three-dimensional silk medical implant product, and wherein the degummed three-dimensional silk medical implant product has a sericin content of below 0.1% (w/w) and a thickness of at least 0.5 mm.

2. Method according to claim 1, wherein the degumming step is performed by contacting the silk product formed with a borate buffer comprising-sodium borate or boric acid.

3. Method according to claim 1, wherein ethanol is used in an aqueous solution containing 1 to 98% (v/v) ethanol.

4. Method according to claim 1, wherein borate is used in an aqueous solution containing 10 to 2000 mM borate.

5. Method according to claim 1, wherein formation of a three-dimensional silk product is performed by weaving, braiding, knitting or pressing.

6. Method according to claim 1, wherein the native silk fibres are fibres from silkworm (*Bombyx mori*) cocoon.

7. Method according to claim 1, wherein the silk medical implant product formed is a stent, a nerve conduit, a hernia meshwork, a ligature, scaffolds for tendon, trachea or bronchi, or cartilage and bone scaffolds.

8. Method according to claim 1, wherein the three-dimensional silk product formed is a cell substratum.

9. Method according to claim 1, wherein the degumming step is carried out at a temperature of 20 and 100° C.

10. A degummed three-dimensional silk product medical implant, obtainable by a method according to claim 1.

11. The degummed three-dimensional silk product medical implant according to claim 10, wherein the product is a matrix scaffold, for medical use, for cell attachment, spreading, growth and differentiation.

12. The degummed three-dimensional silk product medical implant according to claim 10 wherein the smallest dimension is not less than 1/100 of the largest dimension.

13. The degummed three-dimensional silk product medical implant according to claim 10 wherein the two smaller dimensions have a ratio of 1:1 to 1:5.

14. The degummed three-dimensional silk product medical implant according to claim 10 wherein the diameter of the product in the smallest dimension is at least 1.0 mm.

* * * * *